(12) United States Patent
Dorn et al.

(10) Patent No.: US 7,550,001 B2
(45) Date of Patent: Jun. 23, 2009

(54) STENT DELIVERY DEVICE AND METHOD FOR STENT DELIVERY

(75) Inventors: Jürgen Dorn, Neulussheim (DE); Michael Vogel, Karlsruhe (DE)

(73) Assignee: C. R. Bard, Inc., Murray Hill, NJ (US)

(*) Notice: Subject to any disclaimer, the term of this patent is extended or adjusted under 35 U.S.C. 154(b) by 1002 days.

(21) Appl. No.: 10/476,351

(22) PCT Filed: Apr. 29, 2002

(86) PCT No.: PCT/EP02/04727

§ 371 (c)(1),
(2), (4) Date: May 7, 2004

(87) PCT Pub. No.: WO02/087470

PCT Pub. Date: Nov. 7, 2002

(65) Prior Publication Data

US 2004/0181239 A1    Sep. 16, 2004

(30) Foreign Application Priority Data

Apr. 30, 2001  (GB) .................................. 0110551.9

(51) Int. Cl.
*A61F 2/06* (2006.01)
(52) U.S. Cl. .................................................. 623/1.12
(58) Field of Classification Search ............... 606/108, 606/200, 192–198, 205–209, 99, 86 A, 86 R; 623/1.11, 1.12, 902, 903, 2.11, 6.12; 600/585; 604/523, 528
See application file for complete search history.

(56) References Cited

U.S. PATENT DOCUMENTS 4,256,113 A * 3/1981 Chamness .................... 606/47
4,580,568 A    4/1986 Gianturco
5,346,498 A * 9/1994 Greelis et al. ............... 606/108
5,433,723 A    7/1995 Lindenberg et al.
5,443,477 A * 8/1995 Marin et al. ................. 606/198
5,466,221 A * 11/1995 Zadini et al. ................. 600/18
5,573,530 A * 11/1996 Fleury et al. ................... 606/1
5,683,451 A    11/1997 Lenker et al.

(Continued)

FOREIGN PATENT DOCUMENTS

DE    A-44 20142 A1    12/1995

(Continued)

*Primary Examiner*—Anhtuan T. Nguyen
*Assistant Examiner*—Elizabeth Houston

(57) ABSTRACT

The present invention relates to a method and device for releasing into the body from a delivery system a medical prosthesis mounted on the delivery system and held by a constraint in a constrained delivery disposition. The device comprises a first hub for the delivery system, a second hub for an elongate element to connect the device to the prosthesis constraint, a track for the second hub to advance along, from a starting point corresponding to constraint of the prosthesis, to a finishing point corresponding to separation of the prosthesis and constraint, ratchet means to advance the second hub progressively, from the starting point to the finishing point, in a plurality of actuation strokes, and a full stroke actuator to advance the second hub all the way from an intermediate point on the track to a finishing point in one single stroke of the actuator, the intermediate point being selectable by the user within a portion of the track which extends over at least half the length of the track.

27 Claims, 2 Drawing Sheets

U.S. PATENT DOCUMENTS

| | | | |
|---|---|---|---|
| 5,707,376 A * | 1/1998 | Kavteladze et al. | 623/1.11 |
| 5,738,667 A | 4/1998 | Solar | |
| 5,906,619 A | 5/1999 | Olson et al. | |
| 5,944,727 A * | 8/1999 | Ahari et al. | 606/108 |
| 5,968,052 A * | 10/1999 | Sullivan et al. | 623/1.11 |
| 6,203,550 B1 * | 3/2001 | Olson | 606/108 |
| 6,238,402 B1 * | 5/2001 | Sullivan et al. | 606/108 |
| 6,319,262 B1 * | 11/2001 | Bates et al. | 606/127 |
| 6,391,051 B2 * | 5/2002 | Sullivan et al. | 623/1.12 |
| 6,514,261 B1 * | 2/2003 | Randall et al. | 606/108 |
| 6,599,296 B1 * | 7/2003 | Gillick et al. | 606/108 |
| 6,660,031 B2 * | 12/2003 | Tran et al. | 623/1.12 |
| 6,755,854 B2 * | 6/2004 | Gillick et al. | 623/1.11 |
| 6,866,669 B2 * | 3/2005 | Buzzard et al. | 606/108 |
| 6,884,259 B2 * | 4/2005 | Tran et al. | 623/1.12 |
| 6,911,039 B2 * | 6/2005 | Shiu et al. | 623/1.12 |
| 6,939,352 B2 * | 9/2005 | Buzzard et al. | 606/108 |
| D576,725 S * | 9/2008 | Shumer et al. | D24/133 |
| 2002/0004663 A1 * | 1/2002 | Gittings et al. | 606/153 |
| 2003/0074045 A1 * | 4/2003 | Buzzard et al. | 623/1.11 |
| 2003/0167060 A1 * | 9/2003 | Buzzard et al. | 606/108 |

FOREIGN PATENT DOCUMENTS

| | | |
|---|---|---|
| DE | 199 36 059 A1 | 2/2001 |
| EP | 0 436 303 A1 | 7/1991 |
| EP | 0 564 894 A1 | 10/1993 |
| EP | 0 611 556 A1 | 8/1994 |
| EP | 0 630 657 A1 | 12/1994 |
| EP | 0 699 451 A2 | 3/1996 |
| EP | A-747 021 A2 | 12/1996 |
| EP | 1 095 634 A2 | 5/2001 |
| WO | WO 98/12998 A1 | 4/1998 |
| WO | WO 98/23241 A2 | 6/1998 |
| WO | WO 99/04728 A1 | 2/1999 |
| WO | WO 99/25280 A1 | 5/1999 |
| WO | WO 99/44541 A1 | 9/1999 |
| WO | WO 99/47075 A1 | 9/1999 |
| WO | WO 99/51167 A3 | 10/1999 |
| WO | WO 00/00104 A1 | 1/2000 |
| WO | WO 00/18330 A1 | 4/2000 |
| WO | WO 00/71059 A1 | 11/2000 |
| WO | WO 00/78248 A1 | 12/2000 |
| WO | WO 01/34061 A1 | 5/2001 |
| WO | WO 03/002020 A2 | 1/2003 |

* cited by examiner

STENT DELIVERY DEVICE AND METHOD FOR STENT DELIVERY

BACKGROUND

1. Field

This invention relates to devices and methods for endoluminal delivery of a medicinal prosthesis, such as a stent.

2. Description of Related Art

The device is particularly applicable to the release into the body of a self-expanding stent, such as one made from nickel-titanium shape memory alloy. Self-expanding stents usually have a basically cylindrical form prior to deployment and it is conventional to deploy these stents with a system having two components. One of these components is a sleeve or sheath which surrounds the stent and constrains it to a radially compact disposition. The other component is a so-called "pusher" which is located inside the constraining sleeve and bears against a surface of the stent. Deployment of the stent is then accomplished by proximal withdrawal of the sleeve relative to the pusher. The pusher maintains the stent in a location relative to the target site of surgery. The proximal withdrawal of the sleeve progressively releases the stent, first at its distal end and then progressively proximally along the length of the stent until, when the distal end of the sleeve is proximal of the proximal end of the stent cylinder, the stent is fully deployed. At this point, the sleeve and pusher delivery system can be withdrawn proximally out of the body, leaving the stent, expanded, in the desired location.

An early disclosure of such a system can be found in Gianturco U.S. Pat. No. 4,580,568.

Radiopaque markers on the stent delivery system (sometimes supplemented by markers on the stent itself) are used to enable radiologists to visualise the location of the stent in the body. Furthermore, the stent delivery system is used as a conduit for filling the bodily lumen to be stented with radiopaque fluid, to enable the radiologist to pinpoint the location of the stenosis or other surgical site where the stent is to be placed. It is then the task of the medical practitioner performing the stenting procedure to bring the radiopaque stent markers into the desired relationship with the site of surgery as indicated by the radiopaque fluid.

Placement of the stent exactly as required is not without its difficulties. There is a need for a delivery system which a medical practitioner can manipulate manually with enough precision to bring the stent reliably into the desired location relative to the surgical site. It will be appreciated that stent delivery systems are commonly of a length around 130 cm and are controlled from the end opposite that in which the stent is carried. Thus, the medical practitioner is to some extent handicapped by having to work at considerable distance from the stent itself.

Stents come in many different lengths. However, for all but the shortest stent length, two phases are typical in a self-expanding stent deployment sequence.

In a first phase, initial proximal withdrawal of the surrounding sleeve releases the distal end of the stent so that this part of the stent length begins to make contact with the bodily lumen which defines the site of surgery. This first phase is characterised in that the stent is still bound to the delivery system and not to the bodily lumen. However, at the end of the first phase, enough of the length of the stent has expanded into contact with the lumen wall to fix the position of the stent relative to the lumen wall. At this point, the stent is bound to both the delivery system and the bodily lumen wall, so that any axial movement of the delivery system relative to the bodily lumen is liable to cause injury to the lumen wall.

The second phase of stent deployment is what follows thereafter, namely, the remainder of the proximal movement of the sheath to release the remaining length of the stent into the bodily lumen. It will be appreciated that any axial stress on the deployed portion of the length of the stent during deployment will transmit to axial stress on that part of the bodily lumen which is in binding engagement with the stent, with the consequence that lumen wall supported by the stent remains in tension and under stress after the stent has been fully deployed. This unwanted axial stress in the bodily tissue could be severely deleterious to the patient in one way or another and is normally to be avoided.

There are proposals in the patent literature for placement of self-expanding stents by progressive distal advancement of a surrounding sheath, to release the stent, proximal end first, terminating at the distal end of the stent. It will be appreciated that this is possible because the radial expansion of the stent opens up a lumen big enough for proximal withdrawal of the sheath from a position distal of the expanded stent. The discussion of axial stresses can be applied, mutatis mutandis, to these configurations proposed in the patent literature, in which the proximal end of the stent is deployed first.

Also previously proposed are combinations of constraining sheaths which withdraw from the stent simultaneously proximally and distally, from a starting point intermediate the ends of the stent, in order to deploy the stent first from a mid part of its length, and terminating with deployment of both the proximal and distal ends of the stent. Even in such systems, the concerns about axial stresses still apply. Therefore, in this specification, although the detailed description is of a system arranged in the usual way, with proximal withdrawal of a surrounding sleeve, it is to be understood that the principles of the invention is also applicable to systems involving distal withdrawal of a surrounding sheath.

For a disclosure within the state of the art of a system which distinguishes between the initial phase of stent deployment and the subsequent phase in which the remainder of the length is deployed, reference is made to WO 99/04728. In this disclosure, it is proposed to use a stent delivery system which is characterised by an initial mechanical advantage for the initial stages of stent deployment, which is large enough to overcome static frictional forces between the stent and the surrounding sheath and to allow the initial part of the length of the stent to be deployed slowly and precisely. Once the sheath has begun sliding over the stent length, and an end of the stent has expanded to engage the surrounding luminal wall, a different and lower mechanical advantage is activated, to withdraw the sheath proximally at a rate more rapid than that characteristic of the initial phase of stent deployment.

The state of the art offers various configurations for the control devices for stent delivery devices from which individual practitioners may choose to fit their particular manual skills best.

WO 99/04728, mentioned above, offers the practitioner a knurled rotatory actuation element whereas WO 00/18330, DE-A-44 20142 and WO 98/23241 are examples of pistol grip devices in which deployment is accomplished by a form of squeeze handle or trigger. See EP-A-747 021 and U.S. Pat. No. 5,433,723 for other examples of rotary stent release devices.

Another approach to the accomplishment of a controlled release of a self-expanding stent can be found in U.S. Pat. No. 5,683,451, the approach relying on so-called runners which lie between the stent and a surrounding sheath. At the proximal end of the delivery system, a follower receives a hub at the proximal end of the surrounding sheath and rotation of a handle causes rotation of a threaded shaft, along which the follower advances, to carry the proximal hub of the sheath in a proximal direction to release the stent.

SUMMARY OF THE INVENTION

This invention relates to a device for releasing into the body from a delivery system a medical prosthesis mounted on the delivery system and held by a constraint in a constrained delivery disposition. The illustrative embodiment of the device comprises a first abutment for the delivery system, a second abutment for an elongate element to connect the device to the prosthesis constraint, a track for the second abutment to advance along, from a starting point corresponding to constraint of the prosthesis, to a finishing point corresponding to separation of the prosthesis and constraint, and ratchet means to advance the second abutment progressively, from the starting point to the finishing point, in a plurality of actuation strokes. According to the more general aspects of the present invention there is provided a device and method for releasing into the body from a delivery system a medical prosthesis mounted on the delivery system, characterised by a full stroke actuator, to advance the second abutment all the way from an intermediate point on said track to said finishing point in one single stroke of the said actuator, the intermediate point being selectable by the user within a portion of the track which extends over at least half the length of the track.

We have found that a release device which embodies both a ratchet means and a full stroke actuator is one which allows a range of individual medical practitioners, all of whom have their own preferred techniques for precise stent deployment, to practice their skilled techniques in the way that suits them best, to lay down an initial part of the length of a stent in a precise location in a bodily lumen, and then to complete the deployment of the length of the stent in a way which is so accurately and precisely controlled that the practitioner can satisfactorily avoid imposing unacceptable axial stresses on the tissue being stented.

In one aspect of the invention, the device offers the medical practitioner a trigger for successive pumping to withdraw the stent-surrounding sheath in proximally stepwise increments, together with a slider which allows the operator to withdraw the sleeve in one stroke. Thus, the trigger provides the ratchet means of the invention and the slider provides the full stroke actuator of the invention. The inventor envisages that it will be convenient for many practitioners to utilise the trigger during the first phase of stent deployment and then, when satisfied that the stent is placed within the bodily lumen as desired, witch from the trigger to the slider in order to deploy the remaining length of the stent with as much fingertip sensitivity as possible, thereby to minimise the imposition of unwanted stresses on the bodily tissue.

Accordingly, in another aspect of the invention, there is provided a method for releasing into the body from a delivery system a medical prosthesis mounted on the delivery system and held by a constraint in a constrained delivery system, the method comprising a first release phase characterised by stepwise release of a first portion of the prosthesis, by successive actuation strokes of a ratchet means, followed by a second phase of release of the prosthesis, characterised by a single stroke of a full stroke prosthesis release actuator.

In a presently preferred embodiment of the invention a collapsible connection is provided between the trigger and the slider, to allow the slider to approach the trigger from any position along its sliding length, without the need to actuate the trigger at any point during withdrawal of the stent sheath.

This is conveniently accomplished by the provision of a collapsible line having one end connected to the shaft of a windlass, and the other end pulling on the sheath, the windlass reeling in the line, this reeling in being accomplished by successive passes of a toothed ratchet segment over the toothed circumference of a windlass drive gear, each pass being achieved by a squeeze of the trigger. Conveniently, the end of the line is connected to the slider. If the slider itself is gripped by the medical practitioner, and urged towards the windlass shaft, the line can collapse as the slider approaches the windlass.

It should be understood that the principles of the invention are not limited to the preferred embodiment and that other mechanisms may be provided that are based on those principles.

BRIEF DESCRIPTION OF THE DRAWINGS

For a better understanding of the invention, and to show an exemplary arrangement by which the same may be carried into effect, reference will now be made, by way of example, to the accompanying drawings, in which.

DETAILED DESCRIPTION OF A PREFERRED EMBODIMENT

Figure 1:
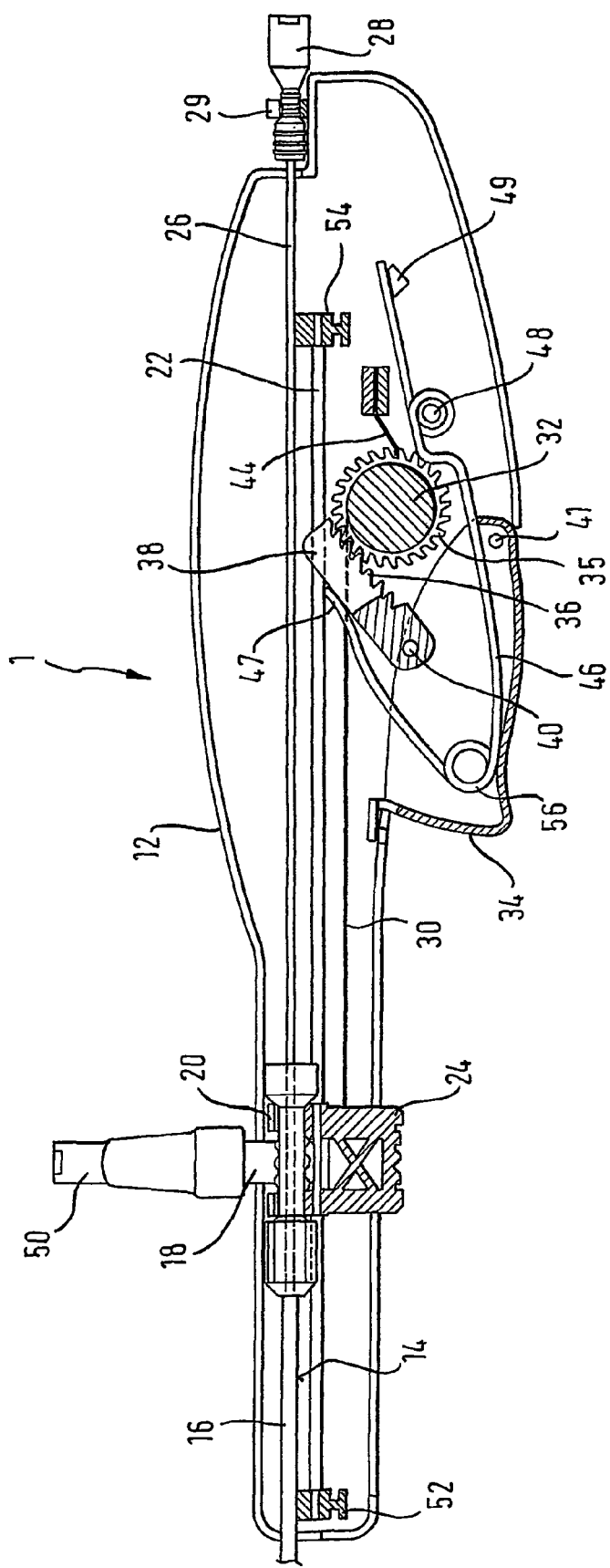
FIG. 1 is a longitudinal mid-section through a hand-held device in accordance with the present invention.

The drawings are of a preferred embodiment of the invention and FIG. 1 shows one half 12 of a moulded housing of which the other half lies above the plane of the drawing.

The two housing halves define, in an assembled state, a track 14 in which can be laid the proximal end of a co-axial stent delivery device having an outer tube 16. Track 14 is formed by mating axial recesses in the two housing halves, resulting in a semi-circular channel open to the upper end in FIG. 1 of the housing.

The proximal end of the outer tube 16 carries a hub 18 which is received within a yoke 20 of a slider 24 which itself runs on a pair of rails 22. The rails 22 are not integral moulded parts of the housing and are held in place by advancing a first one of the rails through a hole (not shown in FIG. 1) and through fixing part 52 and feed hole in slider 24 at the distal end of the housing and into blind hole at fixing point 54 distal from the proximal end of the housing. The distal end of the rail is then bonded to the housing or fixing part 52 using a ultrasonic fusion technique. The two housing halves are then assembled and the other one of the rails is fed through another hole in the distal end of the other housing half, inserted through a feed hole in the slider 24 and pushed into another blind hole at fixing point 54. The distal end of the second rail is also bonded to the housing using an ultrasonic fusion technique Instead of ultrasonically bonding the distal ends of the rails 22 to the housing, they may equally well be adhesively bonded thereto. Although not shown in FIG. 1, rails 22 may also be an integral part of the housing 12. The length of the rails 22 may extend along the entire length of the housing 12, but is at least equal the axial length of the stent to be deployed.

Markers also may be provided on the rails, provided the housing is made of a transparent material, and on the slider to indicate the length of proximal withdrawal of the outer tube 16 with respect to the position of the stent. If, for example, a marker on the slider 24 lines up with a proximal-most marker provided on one of the rails 22, this gives the medical practitioner an indication that the stent has been fully released. The slider 24 protrudes to the outside of the housing 12 at the lower end thereof in FIG. 1, enabling a person to manually urge the slider 24 along the length of the rails 22, when appropriate. The protrusion length of the slider 24 may conveniently be sufficient to be grasped by the thumb and the index finger for optimum handling of the slider.

The inner element 26 of the co-axial delivery device is a rod, or hypo-tube, or like element which extends proximally along the track 14 to a proximal hub 28 which is captivated within the proximal end of the housing 12 and so cannot move proximally or distally once the co-axial delivery device is set within the track 14. Since the opposite end of the rod 26, that is, its distal end, is normally defining the proximal end of the stent to be delivered, the length of the rod 26 defines the distance separating the proximal end of the housing 12, where the hub 28 is captivated, and the proximal end of the stent being delivered. Hub 28 is clipped into engagement with the housing at fixing point 29. Other ways of attaching hub 20 to the proximal end of housing 12 are contemplated and will be apparent to those skilled in the art, such as a yoke.

The body 12 contains actuating elements to draw the slider 24 in a controlled way from the distal end of the rails 22 towards their proximal ends. This proximal sliding movement draws hub 18 proximally, and so draws outer tube 16 of the delivery device proximally. Such a movement would be useful, for example, to release a self-expanding stent from within the distal portion of the tube 16.

To effect a controlled proximal movement of the slider 24, a collapsible line in the form of a pull wire 30 runs from the slider 24 to a windlass or take-up reel shaft 32 which is adjacent a trigger 34 mounted to the housing 12. The reel shaft 32 carries a toothed gear 35, and the teeth engage with complementary teeth 36 on an elongate ratchet element 38 itself pivotably mounted at an axis 40 to the trigger 34. The trigger 34 is mounted in a recess within the housing 12 and is held in place as soon as the two housing halves are assembled.

Trigger 34 is biased to a rest position as shown in FIG. 1 by a leaf spring 46 which is pivotally mounted to the housing 12 at a mounting pin 48. One end 47 of the leaf spring 46 co-operates with the elongate ratchet means 38 and is movable thereon. The other end, beyond mounting point 48 bears against support 49 and is free to move thereon. Between the pivot 48 and the distal end of leaf spring 46 making contact with the ratchet element 38, the wire used for the leaf spring is turned into a helical spring 56. The helical spring serves for optimising the spring-characteristic forces bearing on the ratchet element 38. From portion 56 which establishes the helical spring, the leaf spring essentially follows the contour of the interior of the trigger until another helically turned portion follows, wrapping around the mounting pin 48. At this point, the leaf spring is pivotally mounted to the housing. Thus, when pushing the trigger 34 upwards, the support 49 resists pressure from one end of the spring 46, while the other end of leaf spring 46 making contact with ratchet element 38 is free to follow the movement of the trigger 34. Subsequent to actuation of the trigger, leaf spring reaction on support 49 urges trigger 34 to its rest position while maintaining contact with the ratchet element 38.

Successive pumps on the trigger 34 to move the trigger upwards in FIG. 1, against the bias of leaf spring 46, cause successive corresponding passes of the ratchet element 38 across the rotational axis 42 of the take-up reel shaft 32, causing the shaft 32 to rotate incrementally clockwise, as shown in FIG. 1. Movement of the trigger 34 upwards cause distal end 47 of leaf spring 46 to slide along the surface of ratchet means 38, never losing contact therewith. Thus, a force constantly applied on the ratchet element 38 by the leaf spring 46 urges ratchet element into engagement with the toothed gear 35, so that controlled proximal withdrawal of outer tube 16 is achieved without the risk of no-load operation of the trigger 34. Note, how the end 47 of leaf spring 46 remote from its mounting point 48 urges the ratchet element 38 into contact with windlass gear wheel 35, but nevertheless allows the ratchet element 38 to return to its start position with the downward movement of the trigger 34. The trigger 34 and ratchet element 38 are helped to return to their original dispositions by the bias spring 46 acting on the trigger 34. Helical spring portion 56 of leaf spring 46 rests on the interior surface of trigger 34, as shown in FIG. 1.

FIG. 1 also shows pivot axis of trigger 34 at pivot point 41. By pushing trigger upwards, trigger slightly rotates around axis 41, thereby moving ratchet element 38 connected with trigger 34 at mounting point 40 upwards and causing windlass gear 35 to rotate clockwise. This clockwise rotation of windlass gear 35 causes pulling on line 30 moving hub 18 and therewith outer tube 16 proximally, resulting in deployment of the stent at the distal end of the co-axial stent delivery device.

A pawl 44 is mounted to the housing 12, and engages successive teeth of the take-up gear 35, to prevent any anticlockwise return movement of the reel 32 as the ratchet element 38 returns to its initial position.

However, pumps on the trigger 34 are not the only way to bring the slider 24 proximally along the rails 22. As mentioned earlier, one can manually grip the slider 24 and urge it proximally along the rails 22, without any contact at all with the trigger 34. In this case, either the pull wire 30 becomes loose and meanders within the housing 12 (that is to say, it collapses), or else, by the provision of a suitable wind-up mechanism or spring (not shown) on the take-up reel 32, any relief of tension in the wire 30 is met with a corresponding clockwise rotation of the reel 32, to take up any slack in the wire 30. Either way, the person delivering the stent has the option of pumping on the trigger 34, or pulling on the slider 24.

The hub 18 is provided with a fluid inlet port 50 in the form of a Luer lock. This is useful for injecting radiopaque fluid into the bodily lumen which is to be stented for the reason explained above. The Luer lock, modified accordingly, is also used to fix the axial position of outer tube 16 in the event the medical practitioner needs to interrupt the release operation of the stent.

Figure 2:
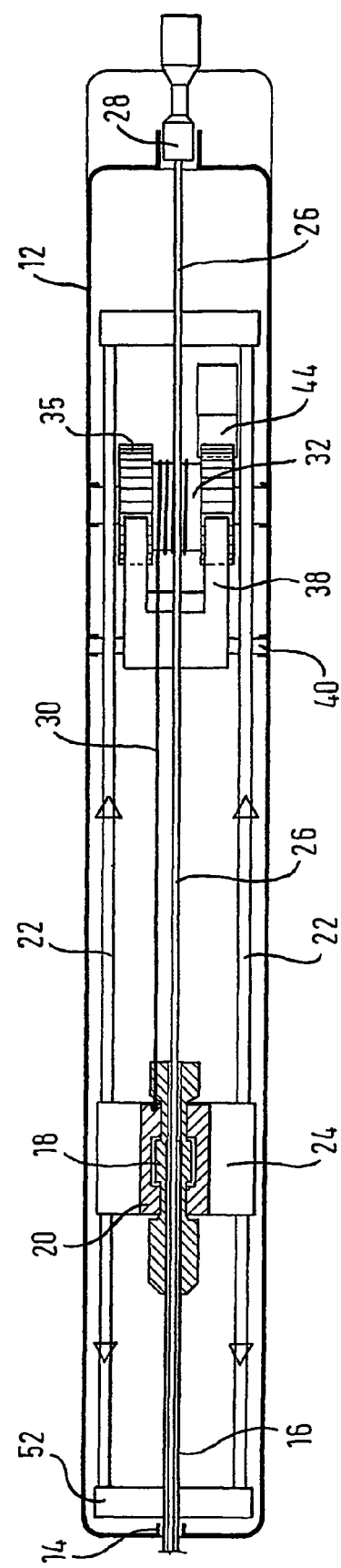
FIG. 2 is a schematic representation, seen from above, of the core components of the FIG. 1 device, enabling the interaction of the different components to be appreciated further.

FIG. 2 is a schematic representation in plan of the device shown in FIG. 1. FIG. 2 shows how line 30 is wound around the windlass gear shaft 32. The winding of line 30 may be achieved by a spring-biased (not shown) reel which reels in any slack in line 30 automatically upon proximal movement of slider 24. According to FIG. 2, the shaft 32 can be formed as a drum flanked at each end by a gear wheel 35, each wheel having its own ratchet element 38, both pivotally mounted to the trigger 34. This assists management of the reeling in of the pull wire 30.

The above description is of a device to fit at the proximal end of a coaxial catheter device for percutaneous transluminal stent delivery. In such systems, it is customary to provide a hub at the proximal end of the two coaxial elements of the system. What is contemplated is that the present device will engage with these two hubs, and allow the usual range of connections to be made to each of the hubs. Thus, for example, it is to be expected that a guide wire will extend proximally from the hub at the proximal end of the inner element of the coaxial system, that the hub of the outer sheath will seal with the inner coaxial element and that it will also have a port arrangement for the admission or withdrawal of liquids from the annular space between the two coaxial elements of the system.

It is the intention that the above described system should have wide application to different stent delivery systems, this being facilitated by provision of easily exchangeable engagement formations in the housing for the respective hubs.

For ease of use, it is contemplated that the housing would display identical left and right sides, a lower edge with the trigger in it, and an upper edge in which the track for receipt of the coaxial stent delivery element is open-topped, so that the stent delivery system can be laid into a recess in the top edge of the housing which extends all the way from one end of the housing to the other. Those skilled in this art will be able to envisage other arrangements.

By providing the trigger 34 with different bores, to mount it on the housing at several different locations relative to the ratchet element 38, a choice of different strokes can be offered, to achieve a desired length of withdrawal of outer sleeve 16 for each stroke of the trigger.

The formation which receive hubs 18 and 28 can be made in the form of resilient clips, so that a variety of different delivery systems can be laid into the track 14.

In fact, the device is designed with flexibility in mind, to enable its use with a range of delivery devices and a range of user characteristics. The housing is deliberately designed symmetrical, that is, not "handed", so it is equally suitable for left-handed and right-handed use.

A stopper may be provided on rails 22 as an indicator or reminder for the medical practitioner that a certain stent length has been deployed and to continue the deployment procedure by manually moving the slider 24 proximally on the rails 22. The stopper may be removed or it may be in the form of a discontinuity on the surface of the rails 22, offering a resistance to slider travel that may easily be overcome manually when continuing the deployment procedure by moving the slider 24 proximally. This provides tactile feedback to the surgeon giving him/her assurance that the stent has been fully deployed.

The materials used for the manufacture of the stent delivery device are, but not limited to, polyoxymethylene (POM), polycarbonate (PC) and other polymer compositions conventionally used for moulding medical devices. Other components, such as the rails and the leaf spring, are made from metal suitable for medical instruments, such as stainless steel with designation 1.4310 or 1.4301. Other materials will be known and readily available to those skilled in the art.

Line 30 is a multifilament polymer-based fibre which gives line 30 greater flexibility than a monofilament line is likely to deliver. This flexibility is important when slider is moved proximally releasing tension in the line which then meanders within the housing.

The invention claimed is:

1. A device for releasing into the body from a delivery system a medical prosthesis mounted on the delivery system and held by a constraint in a constrained delivery disposition, the device comprising:
   a first hub for the delivery system;
   a second hub for an elongate element to connect the device to the prosthesis constraint;
   a track for the second hub to advance along, from a starting point corresponding to constraint of the prosthesis, to a finishing point corresponding to separation of the prosthesis and constraint;
   ratchet means to advance the second hub progressively, from the starting point to the finishing point, in a plurality of actuation strokes; and
   a full stroke actuator disposed distal to the ratchet means, to advance the second hub all the way from an intermediate point on the track to the finishing point in one single stroke of the actuator, the intermediate point being selectable by the user within a portion of the track which extends over at least half the length of the track.

2. Device as claimed in claim 1, wherein the ratchet means comprises a trigger.

3. Device as claimed in claim 2, in which the ratchet means includes a take-up reel.

4. Device as claimed in claim 3, wherein the take-up reel is provided with a pawl to resist reverse movement.

5. Device as claimed in claim 4, wherein a biasing means is provided for biasing the trigger towards a rest position.

6. Device as claimed in claim 5, wherein the biasing means maintains contact of the ratchet means with take-up reel.

7. Device as claimed in claim 5, wherein the biasing means is a leaf spring.

8. Device as claimed in claim 1, wherein the full stroke actuator is a slider.

9. Device as claimed in claim 8, wherein the device includes a housing and the slider protrudes from the housing for manual manipulation.

10. Device as claimed in claim 1, wherein the ratchet means is connected to the second hub by a collapsible element.

11. Device as claimed in claim 10, wherein the collapsible element is a line.

12. Device as claimed in claim 1, wherein the track is provided by a pair of parallel rails.

13. Device as claimed in claim 1, wherein the full stroke actuator is a slider mounted on the track.

14. Device as claimed in claim 13, wherein the device includes a housing and the slider protrudes from the housing for manual manipulation.

15. Device as claimed in claim 1, wherein the ratchet means is connected to the second hub by a collapsible element.

16. Device as claimed in claim 15, wherein the collapsible element is a line.

17. Device as claimed in claim 1, wherein the track is provided by a pair of parallel rails.

18. A device for releasing into the body from a delivery catheter a medical prosthesis mounted on the delivery catheter and held by a constraint of the delivery catheter in a constrained delivery disposition, the device comprising:
   a first hub engageable with a component of the delivery catheter;
   a second hub engageable with an elongate element to connect the device to the prosthesis constraint;
   a track for the second hub to advance along, from a starting point corresponding to constraint of the prosthesis, to a finishing point corresponding to separation of the prosthesis and constraint;
   ratchet means operatively engageable with the elongate element to advance the second hub progressively, from a starting point to the finishing point, in a plurality of actuation strokes;
   a slidable full stroke actuator disposed distal to the ratchet means and associated with the second hub, to advance the second hub all the way from an intermediate point on the track to the finishing point in one single stroke of the actuator, the intermediate point being selectable by the user within a portion of the track which extends over at least half the length of the track.

19. Device as claimed in claim 18, wherein the ratchet means comprises a trigger.

20. Device as claimed in claim 19, in which the ratchet means includes a take-up reel.

21. Device as claimed in claim 20, wherein the take-up reel is provided with a pawl to resist reverse movement.

22. Device as claimed in claim 21, wherein a biasing means is provided for biasing the trigger towards a rest position.

23. Device as claimed in claim 22, wherein the biasing means maintains contact of the ratchet means with take-up reel.

24. Device as claimed in claim 22, wherein the biasing means is a leaf spring.

25. A medical device delivery system comprising:
an inner shaft;
a tubular outer sheath disposed about the shaft, the shaft and sheath being movable relative to each other;
a medical prosthesis disposed within the outer sheath, the inner shaft being engageable with the prosthesis to maintain the position of the prosthesis while the outer shaft is moved in a direction to expose the prosthesis;
a handle device connected to the inner shaft and outer sheath;
the handle device comprising
a first hub engageable with a component of the delivery catheter;
a second hub engageable with an elongate element to connect the device to the prosthesis constraint;
a track for the second hub to advance along, from a starting point corresponding to constraint of the prosthesis, to a finishing point corresponding to separation of the prosthesis and constraint;
ratchet means operatively engageable with the elongate element to advance the second hub progressively, from a starting point to the finishing point, in a plurality of actuation strokes;
a slidable full stroke actuator disposed distal to the ratchet means and associated with the second hub, to advance the second hub all the way from an intermediate point on the track to the finishing point in one single stroke of the actuator, the intermediate point being selectable by the user within a portion of the track which extends over at least half the length of the track.

26. A device as defined in claim 25 wherein the prosthesis comprises an endoluminal stent.

27. A device as claimed in claim 26 wherein the endoluminal stent is self-expanding when released from the constraint.

* * * * *